United States Patent [19]

Gregory et al.

[11] Patent Number: 4,922,020

[45] Date of Patent: May 1, 1990

[54] 1,1,5,5-TETRA(4-AMINOPHENYL)-PENTADI-1,4-ENE COMPOUNDS

[75] Inventors: Peter Gregory, Bolton; Nigel Hughes, Oldham, both of England

[73] Assignee: Imperial Chemical Industries PLC, London, United Kingdom

[21] Appl. No.: 169,573

[22] Filed: Mar. 17, 1988

[30] Foreign Application Priority Data

Mar. 27, 1987 [GB] United Kingdom ............... 8707348

[51] Int. Cl.$^5$ ................ C07C 87/50; C09B 11/02; C07D 277/28; C07D 275/02
[52] U.S. Cl. ........................... 564/330; 546/99; 546/166; 548/181; 548/202; 548/203; 548/214; 564/335
[58] Field of Search ............... 564/315, 330, 335; 546/99, 166, 165; 548/181, 214, 202, 203

[56] References Cited

U.S. PATENT DOCUMENTS

| 3,382,183 | 5/1968 | Donoian et al. | 252/300 |
| 3,647,431 | 3/1972 | Rossi | 96/1.5 |
| 3,677,752 | 7/1972 | Looker et al. | 96/1.6 |
| 3,755,310 | 8/1973 | Rossi | 260/240.9 |
| 4,115,450 | 9/1978 | Garner et al. | 260/558 A |

FOREIGN PATENT DOCUMENTS 0102642 6/1982 Japan .
0093143 5/1986 Japan .

OTHER PUBLICATIONS

European Search Report, Application No. 88302191.7.
Chemical Abstract, vol. 108(10), 10 Mar. 1988.

Primary Examiner—Richard L. Raymond
Assistant Examiner—Peter G. O'Sullivan
Attorney, Agent, or Firm—Cushman, Darby and Cushman

[57] ABSTRACT

A compound of the formula:

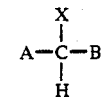

I wherein
A is

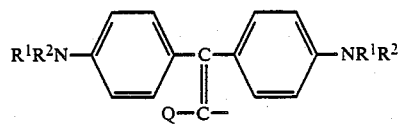

II

B is a group of the formula:

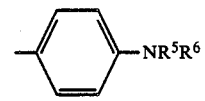

III or

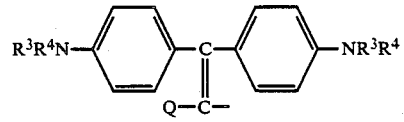

IV when B is of Formula III,
 X is of Formula III;
when B is of Formula IV,
 X is selected from H, phenyl, substituted phenyl, naphthyl, substituted naphthyl, thienyl, substituted thienyl, thiazol-5-yl and substituted thiazol-5-yl in which the substituents are selected from $NR^7R^8$, $NO_2$, $C_{1-4}$-alkyl, $C_{1-4}$-alkoxy, $C_{2-4}$-alkenyl, halogen, cyano and phenyl;
each Q is independently selected from H, $C_{1-4}$-alkyl, phenyl and benzyl;
and wherein each benzene ring in Formulae II, III and IV has no further substituents or carries 1 or 2 further substituents selected from halogen, $C_{1-4}$-alkyl and $C_{1-4}$-alkoxy.

The compound is suitable for use as a charge transport material in organic photoconductors, as a charge control agent in electroreprographic toners and as a color former in pressure sensitive recording materials.

5 Claims, No Drawings

1,1,5,5-TETRA(4-AMINOPHENYL)-PENTADI-1,4-ENE COMPOUNDS

This invention relates to new chemical compounds which are useful as charge transport compounds in photoconductor devices, as colourless, positive-charging, charge control agents in reprographic toners and as colour formers in pressure-sensitive recording material.

The compounds of the invention have the general formula:

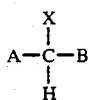   I wherein
A is

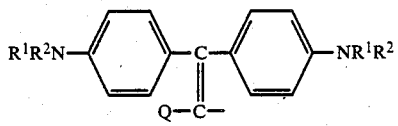   II

B is a group of the formula

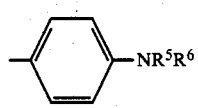   III or

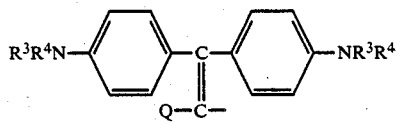   IV when B is of formula III,
X is of Formula III;
when B is of Formula IV,
  X is selected from H, phenyl, substituted phenyl, naphthyl, substituted naphthyl, thienyl, substituted thienyl, thiazol-5-yl and substituted thiazol-5-yl in which the substituents are selected from , NO , $C_{1-4}$-alkyl, $C_{1-4}$-alkoxy, $C_{2-4}$-alkenyl, halogen, cyano and phenyl;
  each Q is independently selected from H, $C_{1-4}$-alkyl, phenyl and benzyl;
  each $R^1$ and $R^2$ is independently H, $C_{1-4}$-alkyl, trimethylene or $C_{1-4}$-alkyl-substituted trimethylene which is also attached to the ortho carbon atom of the adjacent benzene ring; or
  $R^1$ and $R^2$ together with the nitrogen atom to which they are attached form an aliphatic heterocycle;
  each $R^3$ and $R^4$ is independently H, $C_{1-4}$-alkyl, trimethylene or $C_{1-4}$-alkyl-substituted trimethylene which is also attached to the ortho carbon atom of the adjacent benzene ring; or
  $R^3$ and $R^4$ together with the nitrogen atom to which they are attached form an aliphatic heterocycle;
  each $R^5$ and $R^6$ is independently H, $C_{1-4}$-alkyl, trimethylene or $C_{1-4}$-alkyl-substituted trimethylene which is also attached to the ortho carbon atom of the adjacent benzene ring; or
  $R^5$ and $R^6$ together with the nitrogen atom to which they are attached form an aliphatic heterocycle;
  each $R^7$ and $R^8$ is independently selected from H, aryl, $C_{1-4}$-alkyl, substituted $C_{1-4}$-alkyl, trimethylene and $C_{1-4}$-alkyl-substituted trimethylene which is also attached to the ortho carbon atom of the adjacent benzene ring; or
  $R^7$ and $R^8$ together with the nitrogen atom to which they are attached form an aliphatic heterocycle;
and wherein each benzene ring in Formulae II, III and IV has no further substituents or carries 1 or 2 further substituents selected from halogen, $C_{1-4}$-alkyl and $C_{1-4}$-alkoxy.

In the groups of Formulae II and IV it is preferred that each Q is H.

In the compound of Formula I wherein B and X are both of Formula III it is preferred that $R^1$ and $R^2$ are the same and are $C_{1-4}$-alkyl, especially methyl or ethyl. It is preferred that $R^5$ and $R^6$ are the same and are $C_{1-4}$-alkyl, especially methyl or ethyl. However, $R^1$ and $R^5$ may be the same or different and it is preferred that both are methyl or ethyl or that one is ethyl and the other methyl.

In the compound of Formula I wherein B is of Formula IV it is preferred that $R^1$ and $R^2$ are the same and are $C_{1-4}$-alkyl, especially methyl or ethyl. It is preferred that $R^3$ and $R^4$ are the same and are $C_{1-4}$-alkyl, especially methyl or ethyl. However, $R^1$ and $R^3$ may be the same or different and it is preferred that both are methyl or ethyl or that one is ethyl and the other methyl.

When B is of Formula IV it is preferred that X is unsubstituted or substituted by a group $NR^7R^8$. It is further preferred that X is phenyl or substituted phenyl and more especially phenyl carrying a group $NR^7R^8$ in the 4-position relative to the free valency. It is also preferred that $R^7$ and $R^8$, which may be the same or different, are selected from H, phenyl, $C_{1-4}$-alkyl and substituted $C_{1-4}$-alkyl. The substituent on the substituted alkyl group, $R^7$ or $R^8$, is preferably selected from hydroxy, halogen, cyano, aryl, especially phenyl, $C_{1-4}$-alkoxy, $C_{1-4}$-alkoxy-$C_{1-4}$-alkoxy, $C_{1-4}$-alkylcarbonyl, $C_{1-4}$-alkoxycarbonyl, $C_{1-4}$-alkylcarbonyloxy, $C_{1-4}$-alkoxycarbonyloxy and $C_{1-4}$-alkoxy-$C_{1-4}$-alkoxycarbonyl. It is especially preferred that $R^7$ and $R^8$ are both methyl or ethyl. The phenyl group in X may also carry one or two further substituent in the 2 or 2 and 5 positions with respect to the free valency, selected from $C_{1-4}$-alkyl, $C_{1-4}$-alkoxy, halogen and $C_{1-4}$-alkylaminocarbonyl.

The halogen atom or atoms which may be present in the compound of Formula I are preferably chlorine or bromine.

When one or more of the substituents $R^1$, to $R^8$ is trimethylene or $C_{1-4}$-alkyl-substituted trimethylene attached to an ortho carbon atom in the adjacent benzene ring, the compound of Formula I may carry up to four tetrahydroquinolinyl or julolidinyl groups each of which may contain up to 6 alkyl groups, especially methyl. Examples of such systems are tetrahydroquinolin-6-yl and 1,2,2,4-tetrasethyltetrahydroquinolin-6-yl. Heterocyclic groups which may be formed by $R^1$ and $R^2$, $R^3$ and $R^5$ and $R^6$ or $R^7$ and $R^8$, together with the nitrogen atoms to which they are attached, include pyrrolidin-1-yl, piperidin-1-yl, piperazin-1-yl and morpholin-4-yl.

Compounds of Formula I in which B and X are of Formula III may be prepared by condensing an olefin of the formula:

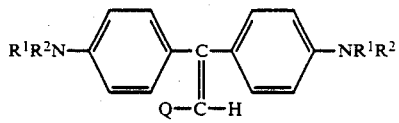

V with a benzhydrol of the formula:

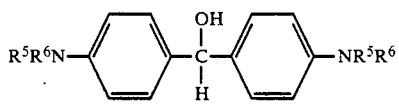

VI wherein the substituents Q, $R^1$, $R^2$, $R^5$ and $R^6$ have the meanings given above, in the presence of a condensing agent, such as 4-toluene-sulphonic acid.

Compounds of Formula I in which B is of Formula IV and X is phenyl carrying a group $NR^7R^8$ in the 4-position with respect to the free valency may be prepared by condensing one mole of an olefin of Formula V and one mole of an olefin of the formula:

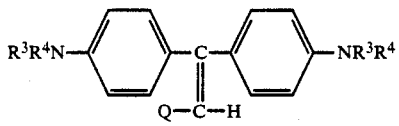

VII with one mole of an aldehyde of the formula:

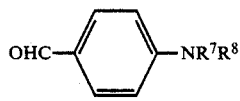

VIII wherein $R^7$ and $R^8$ have the meanings given above, preferably in the presence of a condensing agents, such as 4-toluenesulphonic acid. Equivalent compounds in accordance with Formula I, in which X is one of the other options herebefore described, may be prepared using the same process in which the substituted benzaldehyde of Formula VIII is replaced by another benzaldehyde or a naphthaldehyde, thienaldehyde or thiazolaldehyde.

The compounds of Formula I are especially useful as charge transport compounds (CTC) in organic photoconductor (OPC) devices such as are commonly used in electrophotographic copiers and printers. Such OPC devices generally comprise an electrically conducting substrate carrying a charge generation phase (CGP) and a charge transport layer (CTP) which may be separate or combined in a single phase.

The substrate may be a supportive electrical conducting material, such as a metal support preferably in the form of a drum or a composite material comprising an insulating supporting material such as a sheet of polymeric material, e.g. a polyester sheet or film, coated with a thin film of a conducting material, e.g. a metal such as aluminium, in the form of a drum or a continuous belt.

The CGP may comprise the charge generator alone preferably in the form of a layer deposited on the substrate, or the charge generator may be dispersed in a resin and formed into a layer on the substrate. Examples of suitable resins for use in the CGP are polycarbonate, polyester, polystyrene, polyurethane, epoxy, acrylic, styrene-acrylic, melamine and silicone resins. Where the resin does not have good adhesive properties with respect to the substrate, e.g. a polycarbonate resin, adhesion between the resin and the substrate may be improved by the use of an adhesive resin. Specific examples of suitable resins for use in the CGP are LEXAN 141 Natural (General Electric Plastics, Europe) and Styrene-Acrylate Resin E048 (Synres Nederland BV). A suitable adhesive resin for bonding the charge generating phase to the substrate is VMCA (Union Carbide).

Suitable charge generation compounds for use in the CGP include dyes and especially pigments of various chemical types, for example azo, squaraine, thiapyrilium, phthalocyanine and polycyclic aromatic carbonyl compounds.

The CTP preferably comprises a layer of a resin containing the charge transport material and preferably has a thickness from 1.0 microns ($\mu$) to 50$\mu$ and more preferably from 5.0$\mu$ to 30$\mu$. Examples of suitable resins for use in the CTP include one or more of polycarbonate, polyester, polystyrene, polyurethane, epoxy, acrylic, styrene-acrylic, melamine and silicone resins.

The compounds of Formula I may be included in the CTP and the OPC may be prepared using methods described in the prior art.

The new compounds of the present invention are also suitable as colourless charge control agents (CCA) for electroreprographic toners, especially positive charging toners. The CCA are especially valuable in two component systems (toner+carrier) but are also suitable for one-component toners and liquid toners.

The new compounds of the invention are also useful as colour formers (chromogens) in pressure sensitive recording material and may be used in conventional manner. They may be used in conventional solvents known in the art such as alkylated biphenyls, e.g. isopropyl biphenyl), naphthalenes, e.g. as partially hydrogenated naphthalene, terphenyls (which may be partially or totally hydrogenated), diesters of dicarboxylic acids, e.g. alkyl oxalates and phthalates, and polyhalogenated paraffins, e.g. the various commercially-available polychlorinated mixed paraffin fractions comprising chlorohydrocarbons having chain lengths in the range $C_{10-30}$ and a chlorine content of 20% to 70% by weight. The solution in a suitable organic solvent may be microencapsulated using conventional techniques and the encapsulated system incorporated into pressure-sensitive materials, including materials readable by OCR devices.

Thus, the capsule walls can be formed evenly around the droplets of the colour former solution by coacervation and the encapsulating material can consist of gelatin and gum arabic, as described e.g. in U.S. Pat. No. 2,800,457. The capsules can also be formed from an aminoplast or modified aminoplast by polycondensation, as described in GB No. 989,264, GB No. 1,156,725, GB No. 1,301,052 and GB No. 1,35,124. Other suitable microcapsules are formed by interfacial polymerisation e.g. capsules formed from polyester, polycarbonate, polysulphonamide, polysulphonate, but in particular from polyamide of polyurethane.

The microcapsules containing the compounds of Formula I can be used for the production of a wide variety of known kinds of pressure-sensitive copying material. The various systems differ substantially from one another in the arrangement of the capsules, of the colour reactions, and of the support. A preferred arrangement is that in which the encapsulated chromogenic compound is in the form of a layer on the back of a transfer sheet and the developer is in the form of a layer on the face of a receiver sheet.

Another arrangement of the components is that wherein the microcapsules which contain the chromogenic compound, and the developer, are in or on the same sheet, in the from of one or more individual layers, or are present in the paper pulp.

Conventional co-reactants may be used for the chromogenic compounds of the present invention and as examples there may be mentioned active clays, such as acid clay, attapulgite, zeolite and bentonite; solid organic acids, such as succinic acid, tannic acid and benzoic acid; acidic polymers, such as phenol-formaldehyde, phenol-acetylene, residual acid group-containing styrene-maleic anhydride and salicylic acid-formaldehyde polymers; and heavy metal salicylates, such as zinc salicylate.

The invention is illustrated by the following Examples in which all parts and percentages are by weight unless otherwise stated.

EXAMPLE 1

1,1,3,5,5-Penta(4-[N,N-dimethylamino]phenyl)-pentadi-1,4-ene (PDPP)

1,1-Bis-4'-dimethylaminophenyl)ethylene (2.66g, Michlers Ethylene) and 4-dimethylaminobenzaldehyde (0.75g) were dissolved in ethanol (50 ml) and the solution raised to reflux. 4-Sulphotoluene (0.01g) was added, the mixture stirred under reflux for 2 hours and cooled. The crystalline product was collected by filtration, washed with ethanol and recrystallised from ethyl acetate as a white solid (2g) melting point 218°–219° C. The product has the structure

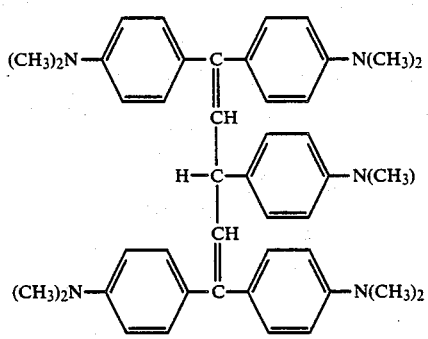

Elementary analysis gives C, 81.3%; H, 8.8% N, 10.7%

$C_{43}H_{53}N_5$ requires C, 80.75%; H, 9.3%; N, 10.95%

Use of PDPP as a colour former in a pressure-sensitive copying paper

The PDPP was incorporated into a pressure sensitive recording material by dissolution in a non-volatile non-polar solvent and encapsulationetc. When the solution was brought into contact with the active mineral surface of a typical receptor sheet by application of pressure, a blue-green image was formed over a period of approximately 1 hour. By reflectance spectroscopy the image had absorption maxima at 610 nm and at 725 nm. Use of PDPP as a charge transport compound in an OPC device A dual layer OPC sheet was prepared on a substrate ob 100 microns aluminised MELINEX by applying an 0.1 μ adhesive layer of VMCA (Union Carbide) followed by a 0.6 μ CGP layer comprising a 1:1 mixture of X-form H₂Pc and LEXAN 141 polycarbonate (as a dispersion in ethylene dichloride). The 14 μ CTP layer comprised a 1:1 mixture of PDPP and LEXAN 141 polycarbonate, applied immediately over the CGP layer, as a dispersion in ethylene dichloride.

The photoconductive properties of this sheet were assessed using a Kawaguchi Electric Works Model SP 428 Electrostatic Paper Analyser in the dynamic mode. The following results were obtained:

| Test Conditions | |
|---|---|
| Corona charge | −6 KV |
| Light intensity (effective) | 5 lux |
| Temperature | 23° C. |
| Relative Humidity | 42% |
| Test Results | |
| Surface charge (V₁) | −850 V |
| % Dark decay (after 5 sec) | 14.1% |
| Sensitivity (lux-sec) | 1.5 lux-sec |
| Residual charge | 25 V |

Use of PDPP as a CCA in reprographic toners

A toner was prepared in the usual manner by hot-melt kneading the following mixed ingredients:

| | |
|---|---|
| CCA (PDPP) | 7.5 g |
| Pigment (MONARCH 1000 carbon black) | 30.0 g |
| Resin (NEOCRYL B1065 styrene/acrylic) | 300.0 g | cooling the melt, crushing the mixture and ball-milling to give the following particle size distribution:

80% >10μ and <35μ

2.6% <5μ.

Two developers were prepared using NV 150 as carrier, one containing 2% toner and the other 10% toner. The triboelectric properties of the developers were measured using a Toshiba TB200 blow-off machine with methylene blue and nigrosine (Spirit Black SB) as controls. The results, in Table 1, show that PDPP confers good positive charging properties to the toner.

TABLE 1

| CCA | 10% Toner | 2% Toner |
|---|---|---|
| PDPP | +10.5 | +4.3 |
| Nigrosine | +13.0 | +12.5 |
| Methylene blue | +6.0 | +4.0 |

PDPP has the added advantages over the industry standard, nigrosine, in that it a single component and non-coloured whereas nigrosine is gross mixture of ill-defined compounds and highly coloured (black); methylene blue is also strongly coloured. Thus, PDPP is especially suitable for use with coloured toners (yellows, magentas and cyans).

EXAMPLE 2

1,1,3,3-tetra(4-[N,N-dimethylamino]phenyl)prop-1-ene (TDPP)

Michler's Ethylene (5g) and of 4,4'-bis-(dimethylamino)-benzhydrol (5g, Michler's Hydrol) were dissolved in methanol (50g) and 4-sulphotoluene (0.1g) was added. After stirring and heating under reflux for 2 hours, the insoluble crude product was isolated by filtration, washed with methanol and crystallised from toluene as a white solid (7g), MP 189°–190° C. It has the structure:

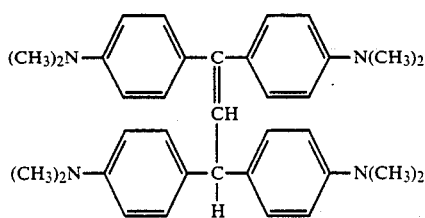

Use of TDPP as a colour former in a pressure-sensitive copying paper

The TDPP was used, as described in Example 1 in place of PDPP, to give an image in a pressure sensitive recording material. The image had an absorption maximum at 615 nm with a shoulder at 720 nm.

Use of TDPP as a charge transport compound in an OPC device

When used as the active ingredient of a CTP as described Example 1 in place of PDPP, the TDPP gave an OPC with the following characteristics:

| | |
|---|---|
| Surface charge (V₁) | −940 V |
| Dark decay (after 5 secs) | 10.6% |
| Sensitivity | 1.5 lux |
| Residual charge | 60 V |

EXAMPLE 3-15

These demonstrate the performance of further compounds of Formula I in positive and negative charging OPC. In the positive charging OPC (Examples 3 to 8), the charge generator was metal free hexadeca(isopropylthio)phthalocyanine and in the negative charging OPC (Examples 9 to 15) the charge generator was dibromoanthanthrone. In Examples 3 to 8 the assessments were carried out with light intensity of 30 lux, a corona charge ob +6 KV, a temperature of 25° C. and relative humidity of 40%. In Examples 9 to 15 the assessments were carried out with light intensity of 30 lux, a corona charge of −6 KV, a temperature of 23° C. and relative humidity of <30%, except for Examples 11 and 15 in which the temperature was 22° C. and the relative humidity was 45%.

The charge transport compounds of the present invention described in Examples 3 to 15 conform to the following formula:

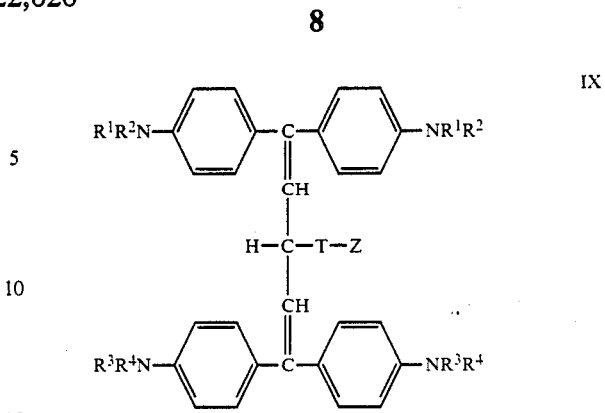

IX

In Examples 3 to 13, T is phen-1,4-ylene, in Example 14, T is naphth-1-yl, and in Example 15, T is 2-methylphen-1,4-ylene (the 2-methyl group being meta to the substituent Z) and the dyes of Formula IX are otherwise defined in Table 2.

TABLE 2

| Ex | R¹ & R² | R³ & R⁴ | Z | V¹ | DD | S | RV |
|---|---|---|---|---|---|---|---|
| | | | Positive Charging | | | | |
| 3 | $CH_3$ | $CH_3$ | $N(CH_3)_2$ | 1460 | 8.9 | 4.2 | 70 |
| 4 | $C_2H_5$ | $C_2H_5$ | $N(C_2H_5)_2$ | 1380 | 10.1 | 3.9 | 90 |
| 5 | $C_2H_5$ | $C_2H_5$ | $NO_2$ | 1360 | 9.6 | 9.9 | 230 |
| 6 | $CH_3$ | $CH_3$ | $NO_2$ | 1290 | 14.0 | 28.5 | 200 |
| 7 | $C_2H_5$ | $C_2H_5$ | H | 1240 | 20.2 | 9.9 | 180 |
| 8 | $CH_3$ | $CH_3$ | H | 720 | — | — | — |
| | | | Negative Charging | | | | |
| 9 | $CH_3$ | $CH_3$ | $N(C_2H_5)_2$ | 760 | 37.5 | 6.0 | 30 |
| 10 | $CH_3$ | $CH_3$ | $N(CH_3)_2$ | 790 | 29.8 | 6.0 | 25 |
| 11 | $C_2H_5$ | $C_2H_5$ | $N(CH_3)_2$ | 780 | 51.3 | 5.0 | 30 |
| 12 | $CH_3$ | $C_2H_5$ | $N(CH_3)_2$ | 820 | 40.2 | 6.0 | 50 |
| 13 | $CH_3$ | $C_2H_5$ | $N(C_2H_5)_2$ | 740 | 50.0 | 5.7 | 25 |
| 14 | $CH_3$ | $CH_3$ | — | 700 | — | — | — |
| 15 | $CH_3$ | $CH_3$ | $N(C_2H_5)_2$ | 830 | 34.9 | 18.5 | 180 |

In Table 2: V¹ is the surface charge (volts). DD is the dark decay (%). S is the sensitivity (lux-sec), and RV is the residual charge (volts)

The compounds shown in Table 2 were made by the process of Example 1 using Michlers ethylene, its tetra-(N-ethyl) analogue or a mixture of these and the appropriate benzaldehyde or naphthaldehyde. Examples 12/13 are mixtures of symmetrical and asymmetrical compounds.

The following compounds are further Examples of the present invention which can be made by the process of Example 1 using Michlers ethylene, its tetra-(N-ethyl) analogue or appropriate derivatives thereof and the appropriate substituted benzaldehyde or thiazolaldehyde. The compounds conform to Formula IX and have the structures shown in Table 3.

TABLE 3

| Ex | R¹ | R² | R³ | R⁴ | T | Z |
|---|---|---|---|---|---|---|
| 16 | $C_2H_5$ | $C_2H_4CN$ | $C_2H_5$ | $C_2H_4CN$ | 1,4-Ph | $N(CH_3)_2$ |
| 17 | $C_2H_5$ | $C_2H_4OCOCH_3$ | $C_2H_5$ | $C_2H_4OCOCH_3$ | 1,4-Ph | $N(C_2H_5)_2$ |
| 18 | $C_2H_4COOCH_3$ | $C_2H_4cOOCH_3$ | $C_2H_4COOCH_3$ | $C_2H_4COOCH_3$ | 1,4-Ph | $N(CH_3)_2$ |
| 19 | $C_2H_5$ | $C_2H_5$ | $C_2H_5$ | $C_2H_5$ | 1,4-Ph | N—$C_2H_5$ \| $C_2H_4OCOCH_3$ |
| 20 | $CH_3$ | $CH_3$ | $CH_3$ | $CH_3$ | 1,4-Ph | $N(C_2H_4COOCH_3)_2$ |
| 21 | $CH_3$ | $CH_3$ | $CH_3$ | $CH_3$ | 1,4-Ph | N—$C_2H_5$ \| $C_2H_4CN$ |
| 22 | $CH_3$ | $CH_3$ | $CH_3$ | $CH_3$ | 1,4-Ph | $COOC_2H_5$ |
| 23 | $CH_3$ | $CH_3$ | $CH_3$ | $CH_3$ | 1,4-Ph | CN |

TABLE 3-continued

| Ex | $R^1$ | $R^2$ | $R^3$ | $R^4$ | T | Z |
|---|---|---|---|---|---|---|
| 24 | $CH_3$ | $CH_3$ | $CH_3$ | $CH_3$ | 1,4-Ph | Cl |
| 25 | $-CH_2CH_2OCH_2CH_2-$ | | $-CH_2CH_2OCH_2CH_2-$ | | 1,4-Ph | $N(CH_3)_2$ |
| 26 | $-CH_2CH_2OCH_2CH_2-$ | | $-CH_2CH_2OCH_2CH_2-$ | | 1,4-Ph | $N(C_2H_5)_2$ |
| 27 | $CH_3$ | $CH_3$ | $CH_3$ | $CH_3$ | 1,4-Ph | $NH-C_6H_5$ |
| 28 | $CH_3$ | $CH_3$ | $CH_3$ | $CH_3$ | 1,4-Ph | $N(C_6H_5)_2$ |
| 29 | $CH_3$ | $CH_3$ | $CH_3$ | $CH_3$ | 2,5-Th | $N(CH_3)_2$ |
| 30 | $CH_3$ | $-C(CH_3)_2CH_2CH-$<br>$\|$<br>$CH_3$ | $CH_3$ | $-C(CH_3)_2CH_2CH-$<br>$\|$<br>$CH_3$ | 1,4-Ph | $N(CH_3)_2$ |

We claim:

1. A compound of the formula:

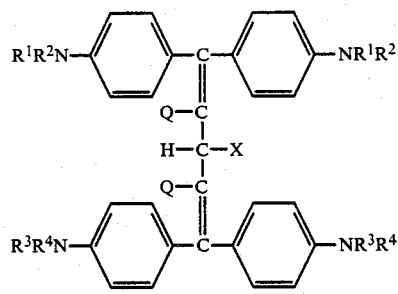

wherein

X is selected from thiazol-5-yl, phenyl, para substituted phenyl, naphthyl, substituted naphthyl, in which the substituents are selected from $NR^7R^8$ and $NO_2$;

each Q is independently selected from H, $C_{1-4}$-alkyl, phenyl and benzyl;

each $R^1$ and $R^2$ is independently H, $C_{1-4}$-alkyl, trimethylene or $C_{1-4}$-alkyl-substituted trimethylene which is also attached to an ortho carbon atom of the adjacent benzene ring;

each $R^3$ and $R^4$ is independently H, $C_{1-4}$-alkyl, trimethylene or $C_{1-4}$-alkyl-substituted trimethylene which is also attached to an othro carbon atom of the adjacent benzene ring;

each $R^7$ and $R^8$ is independently selected from H, aryl, $C_{1-4}$-alkyl, substituted $C_{1-4}$-alkyl, trimethylene and $C_{1-4}$-alkylsubstituted trimethylene which is also attached to an ortho carbon atom of the adjacent benzene ring;

and wherein each benzene ring has no further substituents.

2. A compound according to claim 1 wherein X is of the formula:

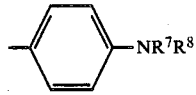

3. A compound according to claim 2 wherein each Q is H, $R^1$ and $R^2$ are methyl or ethyl and $R^3$ and $R^4$ are methyl or ethyl.

4. A compound according to claim 3 wherein $R^7$ and $R^8$ are methyl or ethyl.

5. The compound 1,1,3,5,5-Penta(4-[N,N-dimethylamino]phenyl)-pentadi-1,4-ene.

* * * * *